US010327956B2

(12) United States Patent
MacDonald et al.

(10) Patent No.: US 10,327,956 B2
(45) Date of Patent: Jun. 25, 2019

(54) TRAUMATIC WOUND DRESSING SYSTEM WITH WRAP

(71) Applicants: Avent, Inc., Alpharetta, GA (US); John Gavin MacDonald, Decatur, GA (US); Kelly Dean Branham, Woodstock, GA (US); David William Koenig, Menasha, WI (US); Andrew V. Sweeney, Columbus, OH (US); Stephanie Kute, Columbus, OH (US); Ramanathan S. Lalgudi, Westerville, OH (US)

(72) Inventors: John Gavin MacDonald, Decatur, GA (US); Kelly Dean Branham, Woodstock, GA (US); David William Koenig, Menasha, WI (US); Andrew V. Sweeney, Columbus, OH (US); Stephanie Kute, Columbus, OH (US); Ramanathan S. Lalgudi, Westerville, OH (US); Phillip Andrew Schorr, Atlanta, GA (US); Alison Salyer Bagwell, Alpharetta, GA (US); Brian Joseph Cuevas, Cumming, GA (US); David James McNamara, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 264 days.

(21) Appl. No.: 15/113,112

(22) PCT Filed: Jan. 23, 2015

(86) PCT No.: PCT/US2015/012600
§ 371 (c)(1),
(2) Date: Jul. 21, 2016

(87) PCT Pub. No.: WO2015/112807
PCT Pub. Date: Jul. 30, 2015

(65) Prior Publication Data
US 2017/0007460 A1   Jan. 12, 2017

Related U.S. Application Data

(60) Provisional application No. 61/931,166, filed on Jan. 24, 2014.

(51) Int. Cl.
*A61F 13/00* (2006.01)
*A61F 13/02* (2006.01)
(Continued)

(52) U.S. Cl.
CPC .. *A61F 13/00063* (2013.01); *A61F 13/00068* (2013.01); *A61F 13/0206* (2013.01);
(Continued)

(58) Field of Classification Search
CPC .... A61F 13/0273; A61F 13/551; B65D 81/32
See application file for complete search history.

(56) References Cited

U.S. PATENT DOCUMENTS 4,798,603 A   1/1989   Meyer et al.
4,856,504 A   8/1989   Yamamoto et al.
(Continued)

FOREIGN PATENT DOCUMENTS

JP   2010000159 A   1/2010
WO   WO 2009/102487 A2   8/2009
(Continued)

OTHER PUBLICATIONS

International Search Report and Written Opinion for PCT/US2015/012600, dated Apr. 1, 2015, 6 pages.

*Primary Examiner* — Adam Marcetich
*Assistant Examiner* — Jessica R Arble
(74) *Attorney, Agent, or Firm* — Dority & Manning, P.A.

(57) ABSTRACT

A wound dressing system comprising a wrap and a frangible ampoule is provided. The wrap is configured to contact/surround a wound site and includes an oxygen catalyst. The ampoule includes an oxygen precursor. The catalyst and precursor are configured to form oxygen when combined. A wound dressing system including a container is also pro-
(Continued)

vided that includes a powder, wrap, and frangible ampoule. The powder is disposed within the container, which is configured to allow the powder to be dispersed onto a wound site when activated. The wrap, which may include an oxygen catalyst, is also disposed in the container and is configured to contact/surround the wound site. The ampoule, also disposed in the container, includes a liquid containing an oxygen precursor. The liquid is configured to contact the wrap when the container is activated. Further, the catalyst and precursor are configured to form oxygen when combined.

13 Claims, 4 Drawing Sheets

(51) Int. Cl.
  *A61L 15/44* (2006.01)
  *A61L 15/46* (2006.01)
  *A61L 15/18* (2006.01)
  *A61L 15/58* (2006.01)
(52) U.S. Cl.
  CPC ...... *A61F 13/0226* (2013.01); *A61F 13/0273* (2013.01); *A61L 15/18* (2013.01); *A61L 15/44* (2013.01); *A61L 15/46* (2013.01); *A61L 15/58* (2013.01); *A61F 2013/00314* (2013.01); *A61L 2300/104* (2013.01); *A61L 2300/20* (2013.01); *A61L 2300/212* (2013.01); *A61L 2300/404* (2013.01); *A61L 2400/12* (2013.01)

(56) References Cited

U.S. PATENT DOCUMENTS

| | | |
|---|---|---|
| 5,030,375 A | 7/1991 | Sigl et al. |
| 5,599,585 A | 2/1997 | Cohen |
| 5,730,994 A | 3/1998 | Askill et al. |
| 5,792,090 A | 8/1998 | Ladin |
| 5,807,563 A | 9/1998 | Askill et al. |
| 6,000,403 A | 12/1999 | Cantwell |
| 6,015,764 A | 1/2000 | McCormack et al. |
| 6,020,047 A | 2/2000 | Everhart |
| 6,045,900 A | 4/2000 | Haffner et al. |
| 6,103,647 A | 8/2000 | Shultz et al. |
| 6,111,163 A | 8/2000 | McCormack et al. |
| 6,172,276 B1 | 1/2001 | Hetzler et al. |
| 6,348,258 B1 | 2/2002 | Topolkaraev et al. |
| 6,485,733 B1 | 11/2002 | Huard et al. |
| 6,517,848 B1 | 2/2003 | Huard et al. |
| 6,521,241 B1 | 2/2003 | Minerath, III et al. |
| 6,551,607 B1 | 4/2003 | Minerath, III et al. |
| 6,627,564 B1 | 9/2003 | Morman et al. |
| 6,764,988 B2 | 7/2004 | Koenig et al. |
| 6,767,342 B1 * | 7/2004 | Cantwell ............ A61F 13/00068 424/447 |
| 6,794,024 B1 | 9/2004 | Walton et al. |
| 6,797,856 B1 | 9/2004 | Kolb et al. |
| 6,822,135 B2 | 11/2004 | Soerens et al. |
| 6,887,496 B2 | 5/2005 | Koenig et al. |
| 6,936,035 B2 | 8/2005 | Rake et al. |
| 6,981,967 B2 | 1/2006 | Massengale et al. |
| 7,014,630 B2 | 3/2006 | Rosati |
| 7,160,553 B2 | 1/2007 | Gibbins et al. |
| 7,235,263 B2 | 6/2007 | Koenig et al. |
| 7,268,104 B2 | 9/2007 | Krzysik et al. |
| 7,335,713 B2 | 2/2008 | Lang et al. |
| 7,422,712 B2 | 9/2008 | DeLucia et al. |
| 7,438,711 B2 | 10/2008 | Deniega et al. |
| 7,465,291 B2 | 12/2008 | Massengale |
| 7,527,609 B2 | 5/2009 | Deniega et al. |
| 7,547,302 B2 | 6/2009 | Porto et al. |
| 7,569,045 B2 | 8/2009 | Deniega et al. |
| 7,576,255 B2 | 8/2009 | Gibbins et al. |
| 7,642,397 B2 | 1/2010 | Cohen et al. |
| 7,666,824 B2 | 2/2010 | Krzysik et al. |
| 7,762,045 B2 | 7/2010 | Rosati |
| 7,813,807 B2 | 10/2010 | Franklin |
| 7,959,623 B2 | 6/2011 | Massengale |
| 8,075,537 B2 | 12/2011 | Franklin et al. |
| 8,110,215 B2 | 2/2012 | Koenig et al. |
| 8,166,731 B2 | 5/2012 | Rosati |
| 8,192,841 B2 | 6/2012 | Amundson et al. |
| 8,203,029 B2 | 6/2012 | Gibbons et al. |
| 8,293,965 B2 | 10/2012 | McMaken et al. |
| 8,308,688 B2 | 11/2012 | Valle et al. |
| 8,328,771 B2 | 12/2012 | Massengale |
| 8,361,553 B2 | 1/2013 | Karandikar et al. |
| 8,439,862 B2 | 5/2013 | Massengale |
| 8,475,560 B2 | 7/2013 | Gann et al. |
| 8,505,545 B2 | 8/2013 | Conquergood et al. |
| 8,545,951 B2 | 10/2013 | Yahiaoui et al. |
| 8,551,517 B2 | 10/2013 | Hoffman et al. |
| 8,679,523 B2 | 3/2014 | Gibbins et al. |
| 8,900,209 B2 | 12/2014 | Rosati |
| 8,901,188 B2 | 12/2014 | Karandikar et al. |
| 2001/0031938 A1 | 10/2001 | DeLucia et al. |
| 2002/0006887 A1 | 1/2002 | Radwanski et al. |
| 2002/0022050 A1 | 2/2002 | Anderson et al. |
| 2002/0111576 A1 | 8/2002 | Greene et al. |
| 2003/0040691 A1 | 2/2003 | Griesbach, III et al. |
| 2003/0127767 A1 | 7/2003 | Potts et al. |
| 2003/0203009 A1 | 10/2003 | MacDonald |
| 2004/0010215 A1 | 1/2004 | Gibbins et al. |
| 2004/0120915 A1 | 6/2004 | Yang et al. |
| 2004/0120921 A1 | 6/2004 | Quincy, III et al. |
| 2005/0058711 A1 | 3/2005 | Massengale et al. |
| 2005/0251084 A1 | 11/2005 | Rosati |
| 2005/0267424 A1 | 12/2005 | Eriksson et al. |
| 2006/0003649 A1 | 1/2006 | Runge et al. |
| 2006/0036222 A1 | 2/2006 | Cohen et al. |
| 2006/0036223 A1 | 2/2006 | Baldwin et al. |
| 2006/0067964 A1 | 3/2006 | Koenig et al. |
| 2006/0121101 A1 | 6/2006 | Ladizinsky |
| 2006/0140994 A1 | 6/2006 | Bagwell et al. |
| 2006/0147502 A1 | 7/2006 | Koenig et al. |
| 2006/0200100 A1 | 9/2006 | Rosati |
| 2007/0003603 A1 | 1/2007 | Karandikar et al. |
| 2007/0044801 A1 | 3/2007 | Mathis et al. |
| 2007/0048344 A1 | 3/2007 | Yahiaoui et al. |
| 2007/0048345 A1 | 3/2007 | Huang et al. |
| 2007/0048356 A1 | 3/2007 | Schorr et al. |
| 2007/0134303 A1 | 6/2007 | Yahiaoui et al. |
| 2007/0141130 A1 | 6/2007 | Villanueva et al. |
| 2007/0148459 A1 | 6/2007 | Joseph et al. |
| 2007/0149435 A1 | 6/2007 | Koenig et al. |
| 2007/0254044 A1 | 11/2007 | Karandikar et al. |
| 2007/0293800 A1 | 12/2007 | McMaken et al. |
| 2008/0021373 A1 | 1/2008 | Rosati |
| 2008/0076722 A1 | 3/2008 | Roberts et al. |
| 2008/0108268 A1 | 5/2008 | Little et al. |
| 2008/0132438 A1 | 6/2008 | Hoffman et al. |
| 2009/0014009 A1 | 1/2009 | Chen et al. |
| 2009/0035342 A1 | 2/2009 | Karandikar et al. |
| 2009/0099531 A1 | 4/2009 | Griesbach, III |
| 2009/0099532 A1 | 4/2009 | Cuevas et al. |
| 2009/0202617 A1 | 8/2009 | Ward et al. |
| 2010/0038280 A1 | 2/2010 | Franklin et al. |
| 2010/0041998 A1 | 2/2010 | Postel |
| 2010/0063462 A1 | 3/2010 | Postel et al. |
| 2010/0087946 A1 | 4/2010 | Postel et al. |
| 2010/0190004 A1 | 7/2010 | Gibbins et al. |
| 2011/0135702 A1 | 6/2011 | Hoffman et al. |
| 2011/0184357 A1 | 7/2011 | Robinson et al. |
| 2011/0213319 A1 | 9/2011 | Blott et al. |
| 2011/0257610 A1 | 10/2011 | Franklin |
| 2011/0257617 A1 | 10/2011 | Franklin |
| 2011/0282259 A1 | 11/2011 | Postel et al. |
| 2012/0016306 A1 | 1/2012 | Lee |
| 2012/0059301 A1 | 3/2012 | Franklin |
| 2012/0183674 A1 | 7/2012 | Bonn-Savage et al. |
| 2012/0240728 A1 | 9/2012 | Gann et al. |

(56) References Cited

U.S. PATENT DOCUMENTS

| | | | |
|---|---|---|---|
| 2012/0265124 A1 | 10/2012 | Karandikar et al. | |
| 2012/0322903 A1 | 12/2012 | Karandikar et al. | |
| 2013/0037506 A1* | 2/2013 | Wahlstrom | A61J 1/2093 |
| | | | 215/6 |
| 2013/0085435 A1* | 4/2013 | Murphy | A61K 33/30 |
| | | | 602/46 |
| 2013/0164334 A1 | 6/2013 | Quincy, III et al. | |
| 2013/0396630 | 11/2013 | Franklin | |
| 2014/0046273 A1* | 2/2014 | Kang | A61M 35/003 |
| | | | 604/290 |
| 2014/0276513 A1 | 9/2014 | MacDonald et al. | |
| 2015/0017225 A1* | 1/2015 | Hubbell | A61L 15/64 |
| | | | 424/444 |

FOREIGN PATENT DOCUMENTS

| | | |
|---|---|---|
| WO | WO 2011/091045 A2 | 7/2011 |
| WO | WO 2015/112810 A1 | 7/2015 |

\* cited by examiner

TRAUMATIC WOUND DRESSING SYSTEM WITH WRAP

RELATED APPLICATIONS

The present application is the national stage entry of International Patent Application No. PCT/US2015/012600 having a filing date of Jan. 23, 2015, which claims priority to U.S. Provisional Application Ser. No. 61/931,166, filed on Jan. 24, 2014, both of which are incorporated herein in their entirety by reference thereto.

BACKGROUND

Wound and surgical dressings are often used to treat, cover, and protect wounds and surgical incisions. Wound and surgical dressings come in various forms. For example, for simple cuts, adhesive bandages are typically used. Cotton gauze is also commonly used to cover wounds and surgical incisions. For more serious wounds and surgical incisions, the wound or surgical dressing may include multiple layers of fibrous material with a fluid impervious layer or back sheet to prevent exudates from seeping through the dressing.

Typically, medicaments are often manually applied to the wound or surgical dressing before positioning on a wound or surgical incision. A medicament is a medicinal substance or agent. The medicaments may include, for instance, an antimicrobial agent or antibiotic agent to encourage healing. Antiseptics are also commonly applied to prevent infection.

Catastrophic and traumatic injuries, however, such as limb loss due to bomb blasts, severe burns, and natural disasters require more robust acute treatments to prevent further contamination by debris, mitigate infection, retain body fluids, and prevent heat loss, particularly if surgical care is distant in time or geography.

As such, a need currently exists for a wound dressing system that stabilizes the wound and prevents deterioration of the wound. Such a system can provide a barrier to the environment, can remove or prevent the growth of microorganisms, such as bacteria, and can provide barriers and or absorbency to combat bodily fluid loss, among other desired outcomes of its use.

SUMMARY

Described herein is an innovative medical technology solution particularly useful for service members who suffer the loss of a limb or a severe burn in the field. Currently corpsman and medical personnel are limited to sterile dressings, gauze wraps, ACE™ or other elastic bandages, and in some cases plastic cling-type wrap to dress and protect a severed limb. These types of dressings can provide an exterior covering and keep the mangled limb together, but such dressings do little to promote healing and save valuable tissue. The use of these dressings, coupled with the extended time it often takes to move the casualty to a treatment facility (sometimes 72 hours), result in additional challenges in the form of infection and dead tissue that the battalion surgeons and other medical professionals must address. The traumatic wound dressing system described herein is designed to immediately facilitate the healing process from the point of injury to the initial treatment facility and during lengthy transits from the location of injury to established hospitals. The traumatic wound dressing system described herein is designed to be used in conjunction with a tourniquet to preserve as much of the severed limb as possible, particularly during what is referred to as the 'Golden Hour' after the injury. The traumatic wound dressing system includes a bioactive wrap to prevent infection, oxygen enriched fluid to preserve tissue, and pain medication for comfort. The wound dressing system can also include an exterior conformal cover that protects the wound, contains precious body fluids, helps prevent heat loss, and enables the corpsman to administer additional pharmaceuticals during transit without removal of the entire wrap. It is believed that none of these characteristics are currently available in one device. For instance, currently the M9 Medical Bag contains seven different items to do what the traumatic wound dressing system of the present disclosure does as a single unit. This system will reduce the need for multiple items and ultimately lighten the load the individual corpsman and medic is required to carry. The result will be a lighter load for the corpsman, less loss of valuable tissue, and a more comfortable and stable patient during transit to a medical treatment facility.

In one particular embodiment, the present disclosure is directed to a wrap configured to contact or surround a wound site, the wrap may include an oxygen catalyst and a frangible ampoule including an oxygen precursor/reactant. The oxygen catalyst and the oxygen precursor are configured to form oxygen when combined.

In another embodiment, the wrap can include an inner absorbent layer, where the inner absorbent layer is positioned adjacent the wound site when the wrap is applied to the wound site. In an additional embodiment, the wrap can include an outer protective layer. In yet another embodiment, the wrap can include an elastic layer, a breathable barrier layer, or a combination thereof. In a further embodiment, an end of the wrap can include an adhesive. In yet another embodiment, the oxygen catalyst may be integrated in the wrap. In still another embodiment, the wrap may be a nonwoven composite.

In still another embodiment, the oxygen precursor contemplated by the present disclosure can include a peroxide. The peroxide can include hydrogen peroxide, mannitol peroxide, urea peroxide, an organic peroxide, or a combination thereof.

In a further embodiment, the oxygen catalyst can include a nanoparticle metal, a carbonate, a copper compound, catalase, peroxidase, manganese dioxide, iodide, potassium iodine, or a combination thereof. In one particular embodiment, the nanoparticle metal can include nanoparticle silver.

In another embodiment, the present disclosure is directed to a wound dressing system. The system includes a container; a powder disposed within the container, where the container is configured to allow the powder to be dispersed onto a wound site when the container is activated; a wrap disposed in the container and separated from the powder, where the wrap is configured to contact or surround the wound site; an oxygen catalyst; and a frangible ampoule disposed in the container and including a liquid containing an oxygen precursor, wherein the liquid is configured to contact the wrap upon activation of the container, wherein the oxygen catalyst and the oxygen precursor are configured to form oxygen when combined. In an additional embodiment, the oxygen catalyst may be integrated in the wrap.

In another embodiment, the powder can include a hemostatic agent, an antimicrobial agent, a biotoxin sequestrant, pain medication, a debridement agent, an oxygen catalyst, or a combination thereof.

In still another embodiment, the liquid can include a hemostatic agent, an antimicrobial agent, a biotoxin sequestrant, pain medication, a debridement agent, or a combination thereof.

In a further embodiment, the wrap can include an inner absorbent layer, where the inner absorbent layer is positioned adjacent the wound site when the wrap is applied to the wound site.

In an additional embodiment, the wrap can include an outer protective layer. In yet another embodiment, the wrap can include an elastic layer, a breathable barrier layer, or a combination thereof. In a further embodiment, an end of the wrap can include an adhesive. In another embodiment, the wrap may be a nonwoven composite.

In still another embodiment, the oxygen precursor contemplated by the present disclosure can include a peroxide. The peroxide can include hydrogen peroxide, mannitol peroxide, urea peroxide, an organic peroxide, or a combination thereof.

In a further embodiment, the oxygen catalyst can include a nanoparticle metal such as nanoparticle silver, a carbonate, a copper compound, catalase, peroxidase, manganese dioxide, iodide, potassium iodine, or a combination thereof.

In another embodiment, the present disclosure is directed to a method of a applying a wound dressing system to a wound site. The wound dressing system includes a bioactive powder, a bioactive liquid, and a wrap disposed within a container. The method includes activating the container to disperse the bioactive powder onto the wound site, wherein activating the container ruptures a frangible ampoule inside the container to disperse the bioactive liquid; allowing sufficient time for the wrap to absorb the bioactive liquid, wherein the bioactive liquid includes an oxygen precursor and the wrap includes an oxygen catalyst, wherein oxygen is formed when the bioactive liquid contacts the wrap; and wrapping the wrap around the wound site.

Other features and aspects of the present disclosure are discussed in greater detail below.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

FIG. 1 provides a perspective view in FIG. 1(a) and an exploded view in FIG. 1(b) of one embodiment of a wound dressing system contemplated by the present disclosure;

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects only, and is not intended as limiting the broader aspects of the present disclosure. Additionally, the patents and patent applications described or listed herein are incorporated by reference to the extent they do not conflict herewith.

Figures 1A, 1B:
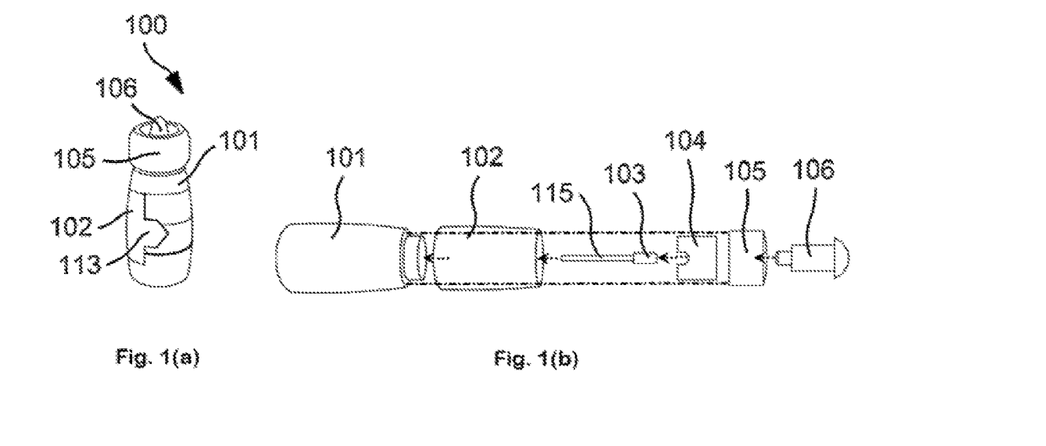
Figure 6:
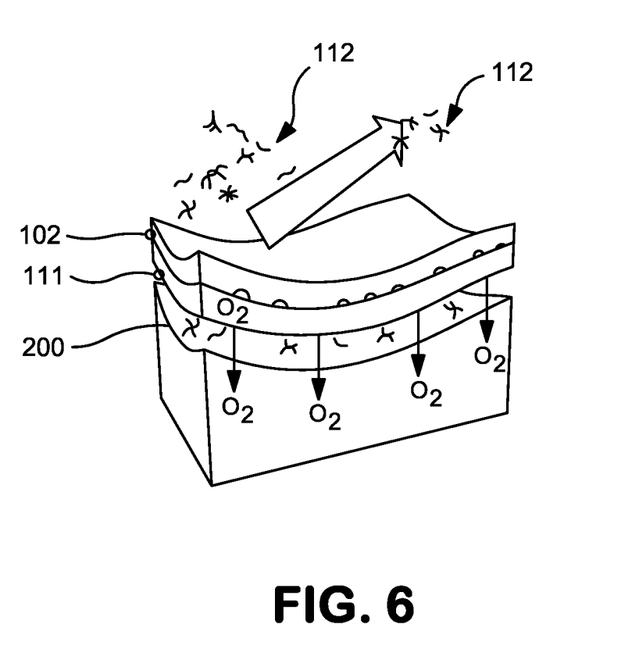
FIG. 6 schematically illustrates the protective and oxygen-generating characteristics of a bioactive wrap contemplated by the wound dressing system of FIG. 1.

The wound dressing system integrates multiple known-effective actives and wound dressing materials and provides the revolutionary addition of healing oxygen in a small, convenient, stable package illustrated in FIG. 1. Currently severely injured limbs are wrapped with gauze and in some cases, covered with plastic wrap. This provides an environment where microbes can flourish and tissue dies. The wound dressing system described herein will not only provide an environment that suppresses microbe proliferation, but it also promotes tissue health via the presence of oxygen. The wound dressing system includes a bioactive wrap that can be in the form of a nonwoven composite or any other suitable material and that provides oxygen-enriched fluid that preserves damaged tissue and a number of other medicaments and substances to preserve tissue and to promote tissue healing. The protective and oxygen-generating characteristics of the wrap are schematically illustrated in FIG. 6 and are discussed in more detail below. Generally, the wrap is contained or stored inside a container such as a protective canister or tube, the powder is disposed in a container or compartment/chamber within or attached to the canister or tube, and the oxygen-generating liquid is contained in an integrated ampoule or other containment device that is frangible and that can be activated during powder release.

As shown in FIG. 1, as packaged, the wrap 102 of the traumatic wound dressing system 100 can be stored in a container such as a canister 101 having a twist cap 105. A portion of the wrap 102 having an adhesive tab 113 can be exposed outside the canister 101. In this manner, the canister 101 can serve as a spool for assisting a user in applying the wrap 102 to a wound site. Contained within the canister 101 is an ampoule 103 containing a bioactive liquid 115 that is surrounded by the remainder of the wrap 102 that is not exposed outside the canister 101. The bioactive liquid 115 contained the ampoule 103 in the center of the canister 101 can be dispensed from the ampoule such that the liquid 115 saturates the wrap 102 surrounding the ampoule 103 before application of the wrap 102 around a wound site. The liquid 115 can be released when the twist cap 105 of the canister 101 is twisted to apply the powder 111. The liquid 103 can contain hemostatic agents, antimicrobial agents, biotoxin sequestrants, pain medication, debridement agents, oxygen precursors (e.g., an oxygen catalyst and a reactant) for oxygen generation, etc.

The wrap 102 can be concentrically rolled around the ampoule 103. The wrap 102 can absorb wound exudate and includes elastic properties to provide enhanced compression, immobilize the wound site, and minimize minor bleeding. Further, the wrap 102 can include or be coated with an oxygen precursor (e.g., a catalyst such as nanoparticle silver) to work in conjunction with the precursors in the liquid 103 to ultimately deliver oxygen to the wound site. In one aspect, the wrap 102 can be from about 10 feet (3.1 meters) to about 15 feet (4.6 meters) in length, such as about 12 feet (3.7 meters) in length, and from about 1 inch (25.4 millimeters)

to about 8 inches (203.1 millimeters) in width, such as about 4 inches (101.6 millimeters) in width, although it is to be understood that the wrap can be any suitable length or width.

Figure 2A:
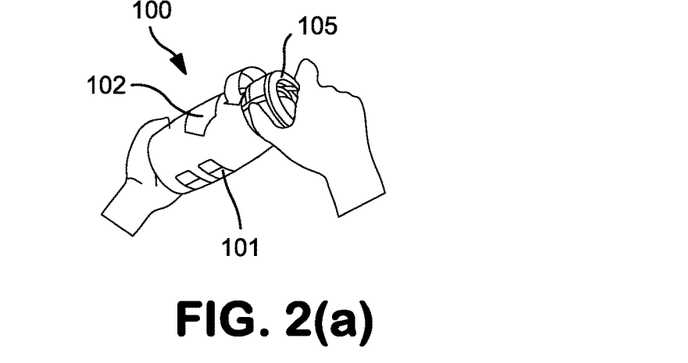
FIGS. 2(a) through 2(g) illustrate the steps for using the wound dressing system of the present disclosure.
Figure 2B:
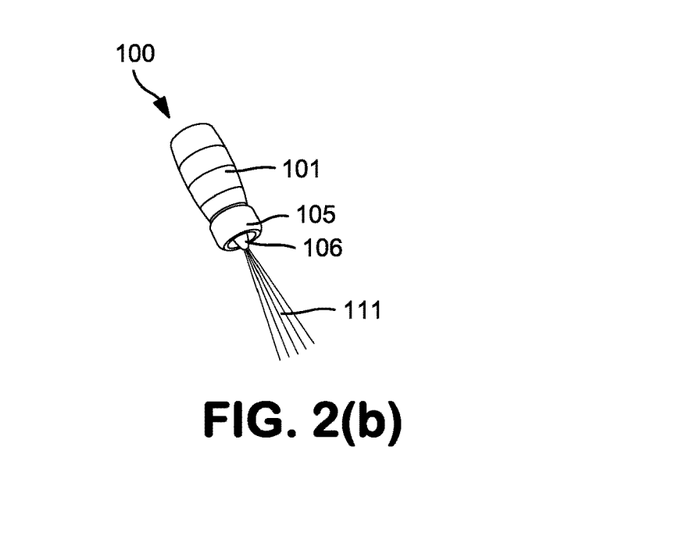
Figure 2C:
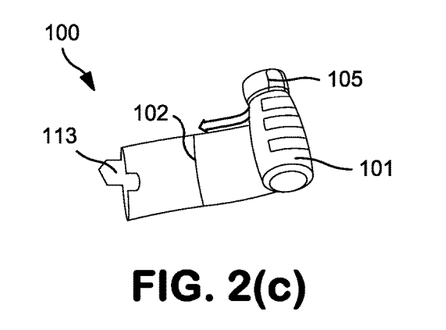
Figure 2D:
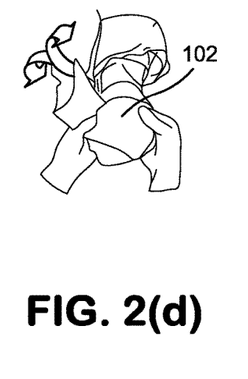
Figure 2E:
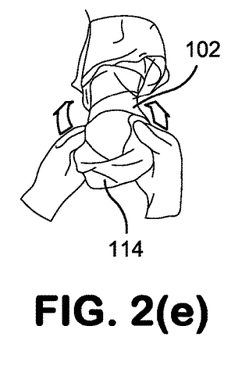
Figure 2F:
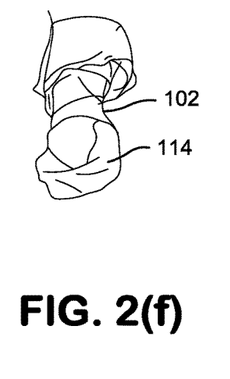

In addition to a liquid-containing ampoule 103 and a wrap 102, also contained within the canister 101 of the traumatic wound dressing 100 is a bioactive powder container 104 in which a bioactive powder 111 (see FIG. 2(b)) can be stored. The powder container 104 can be in the form of a sealed foil pack or any other suitable compartment/chamber. Further, a powder dispenser 106 can be located at an end of the canister 101. The powder dispenser 106 can be in the form of a shaker, nozzle, sprayer, or any other suitable mechanism for dispensing the bioactive powder 111. The bioactive powder 111 can ultimately be applied directly to a wound or wound site by, for instance, rupturing the sealed foil of the powder container 104 when the twist cap 105 is twisted. The bioactive powder 111 can contain hemostatic agents, antimicrobial agents, biotoxin sequestrants, pain medication, debridement agents, an oxygen catalyst for oxygen generation, etc.

It should be understood that when in place around a wound, the traumatic wound dressing system 100 includes the bioactive powder 111, the bioactive liquid 115 that was stored in the ampoule 103, and the wrap 102, while the canister 101, ampoule 103, powder container 104, twist cap 105, and powder dispenser 106 are discarded. The design is focused on storing the bioactive ingredients in methods that insure their necessary activity when the wound dressing system is applied to a wound site and/or the skin surrounding the wound site. Hence, the dry ingredients can be produced as a bioactive powder 111 that is protected in the powder container 104 or other suitable compartment/chamber that can be sealed using foil or any other suitable means. Meanwhile, the liquid ingredients are protected in a foil ampoule 103 or other suitable containment device. As mentioned above, both the powder container 104 and ampoule 103 can be opened at the time of use by twisting cap 105 of the canister 101. In its packaged form, the wrap 102 can be positioned in concentric layers around the ampoule 103 in the wrap canister and designed to quickly absorb the bioactive liquid 115 upon rupture of the ampoule 103. Generally, the bioactive liquid 115 can be absorbed in less than about 1 minute, such as less than about 30 seconds, such as less than about 15 seconds. The wrap 102 can also have sufficient elasticity to provide compression to and help immobilize the damaged area once applied to the wound site. The canister 101, including its twist cap 105, powder dispenser 106, and other components can be manufactured from plastic, rubber, metal, or any other suitable material.

As shown in FIG. 6, when the traumatic wound dressing system is in use and has been applied to a wound site 200, the combination of the coating of the bioactive powder 111 around the wound site 200 and the application of the wrap 102 provides a barrier to prevent or reduce the introduction of microbes 112 or other contaminants into the wound and also provides oxygen-enriched fluid that can preserve damaged tissue. In use, the wound dressing system can also provide a hemostatic agent, a biotoxin sequestrant, a broad spectrum antimicrobial, pain medication, compression, wound exudate absorbency, and a neutral surfactant system to enhance debridement of the wound site once care is rendered at an aid station.

In one example of the use of this traumatic wound dressing system 100 of the present disclosure, a severe limb injury (e.g., avulsion, amputation, laceration, compound fracture, severe burn, degloving, and/or severe abrasion) occurs in theater (i.e., a large area of military operations). A user (e.g., corpsman, medic, first responder, etc.) can then remove the lightweight, compact traumatic wound dressing system of the present disclosure from his/her kit. The user can then assess the wound to determine which components of the wound dressing system are needed and then can apply the various components of the wound dressing system 100 as discussed below and as shown in FIGS. 2(a) through 2(g).

First, as shown in FIG. 2(a), after the user has removed the traumatic wound dressing system 100 from its protective packaging, the user can hold the canister 101 and twist the twist cap 105 to expose the powder 111 (see FIG. 2(b)) contained inside the bioactive powder container 104. For instance, the twisting action peels open the foil seal of the powder container 104 that protects the bioactive powder prior to use. The twisting action also breaks the ampoule 103 located inside the canister 101, which allows the bioactive liquid 115 including oxygen-generating components (e.g., a reactant such as a peroxide) to saturate the portion of the wrap 102 that is concentrically wrapped around the ampoule 103 inside the canister 101.

Next, as shown in FIG. 2(b), the user can squeeze or compress the canister 101 to activate the canister 101 and thus distribute the powder 111 in a controlled manner onto a wound site. The powder 111 can contain oxygen catalysts for use in generating oxygen, as well as hemostatic and antimicrobial components to treat damaged tissue, avoid infection, and prevent further tissue damage. The squeezing action to activate the canister 101 can also rupture the ampoule 103 so that the bioactive liquid 115 can be saturate or coat the wrap 102 inside the canister 101.

Next, as shown in FIG. 2(c)-2(f), the bioactive liquid 115 saturated wrap 102 can be wrapped around a wound. The adhesive strip 113 on the portion of the wrap 102 that is external to the canister 101 prior to use can be used to initially hold the wrap in place on healthy tissue near the wound site to facilitate the wrapping of the wrap 102 around the wound site. Meanwhile, the roll-over feature 114 at the opposite end of the wrap 102 can provide additional coverage over the end of the wound. The bioactive liquid 115 saturated wrap 102 provides compression, helps to immobilize the damaged area, and minimizes minor bleeding. Additionally, the bioactive liquid 115 can provide oxygen, hemostatic, and antimicrobial constituents to the wound site.

Figure 2G:
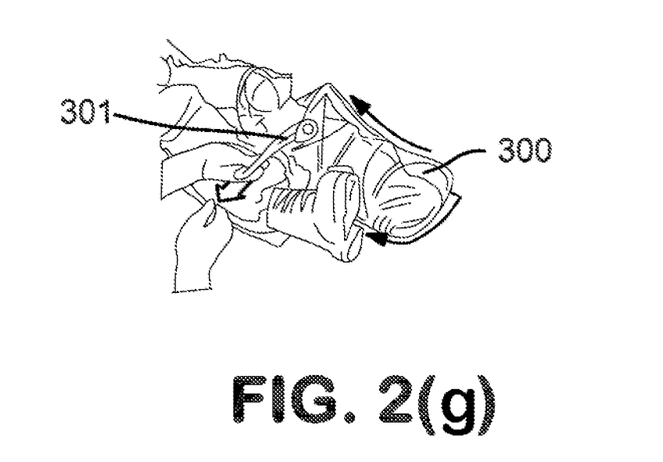

Lastly, as shown in FIG. 2(g), a conformal cover 300 can be placed over the wrap 102 of the traumatic wound dressing system 100 after the wound site has been appropriately wrapped. Once the conformal cover 300 is opened, it can be positioned over the wound site (e.g., a stump portion of an amputated limb), and its cinch straps 301 can then be pulled to secure the conformal cover 300 around the wound site. The multi-purpose conformal cover 300 can protect the wound site in the field environment and can also provide ports for removal of excess fluid from the wound or for the infusion of bioactive liquids or fluids, etc. into the wound site to stabilize and protect the wound site during transport. Integral to the cover is a manual pump and internal distribution capillary to provide bioactive liquids and other medications to the wound for a time period of up to 72 hours.

It should be noted that wound dressing in the field is performed primarily at night, under chaotic conditions, or both. Current systems including multiple, separate items tend to be dumped on the ground or splayed in a dirty environment for quick access. Removal of the wound dressing system of the present disclosure is similar to gauze, and the wrap is single-use only and is disposed of after use. It should also be noted that the bioactive wrap of the present application can be used separately from or in conjunction with the multi-purpose conformal cover described in co-pending U.S. Provisional Application Ser. No. 61/931,186, filed on Jan. 24, 2014. The bioactive wrap 102 and the conformal cover 300 can be packaged separately or together, depending on the intended use.

gentle irrigation of the wound area with saline. Active agents that can be included in the bioactive powder include antimicrobial agents, hemostatic agents, biotoxin sequestrants, pain medication, and debridement agents such as those described in Table 1 and discussed in more detail below.

TABLE 1

Description and Function of Bioactive Powder Components

| Ingredient | Function | Core Technology |
|---|---|---|
| Polyhexamethylene Biguanide (PHMB) | Broad Spectrum Antimicrobial | U.S. Pat. No. 8,551,517<br>U.S. Pat. App. Publication No. 2007/0048345<br>U.S. Pat. App. Publication No. 2010/0190004 |
| Aluminum Chloride, Kaolinite, Mineral Zeolite, or Microfibrillar Collagen | OTC Topical Hemostatic Agents | DRYSOL ™ and XERAC ™ AC by Person & Covey<br>CERTAINDRI ™ by DSE Healthcare<br>AVITENE ™ Flour by Davol<br>HELITENE ™ by Integra<br>INSTAT ™ by Ethicon |
| Lidocaine, Benzocaine, or Prilocaine | OTC Local Analgesic | BIOPELLE ™ by Ferndale Laboratories |
| Chlorhexidine Gluconate (CHG) | Preservative Antimicrobial | U.S. Pat. App. Pub. No. 2007/0048345 |
| Biocompatible Carrier | Rheology Modifier Absorbent Moisture Control | U.S. Pat. No. 7,335,713<br>U.S. Pat. No. 6,822,135<br>U.S. Pat. No. 8,679,523<br>U.S. Pat. No. 8,901,188<br>U.S. Pat. App. Publication No. 2012/265124<br>PCT/US2014/067530<br>Caprolactone Urethane<br>Poly(lactic Acid) Diol Urethane<br>Poly(ethylene glycol) Urethane<br>Hydroxybutyric acid urethane |
| Modified Clay | Rheology Modifier Biotoxin Sequestration | U.S. Pat. No. 6,485,733<br>U.S. Pat. No. 6,517,848 |
| Structured Surfactants | Active Migration Aid Debridement Aid | U.S. Pat. No. 7,666,824 |
| Sodium Carbonate | Neutralizer | — |
| Citric Acid | pH Modifier | — |
| Nanoparticle Metal (e.g., nanoparticle silver) | Antimicrobial and Oxygen Catalyst | U.S. Patent App. Pub. No. 2007/0003603<br>U.S. Pat. No. 8,203,029<br>U.S. Pat. No. 8,361,553<br>U.S. Pat. No. 7,576,255<br>U.S. Pat. App. Pub. No. 2004/0010215 |

The bioactive powder, liquid, and wrap components of the traumatic wound dressing system of the present disclosure are discussed in more detail below.

1. Powder

The bioactive powder can be applied directly to the wound and can include one or more of antimicrobial agents, hemostatic agents, biotoxin sequestrants, pain medication, debridement agents, and oxygen catalysts such as a nanoparticle metal (e.g., nanoparticle silver), a carbonate (e.g., sodium bicarbonate), a copper compound, catalase, peroxidase, manganese dioxide, iodide, potassium iodine, etc. The bioactive ingredients may be incorporated into, integrated with, or included in a biocompatible carrier, and the biocompatible carrier itself may have bioactive properties.

The bioactive powder composition can treat and stabilize damaged tissue, stop bleeding, avoid infection, neutralize biotoxins, and allow for rapid and complete debridement of the wound site at a later time. The powder is uniquely beneficial in that it can be applied to most wound shapes and depths and quickly sets up as a flexible barrier by absorbing the wound exudate and forming a hydrogel seal on the wound bed. The resulting hydrogel can also maintain a good balance of moisture in the wound bed. The hydrogel powder can also deliver antimicrobial agents and/or other bioactives to the wound site for wound preservation and healing. Further, the hydrogel powder can be easily removed by gentle irrigation of the wound area with saline.

a. Antimicrobials

Any suitable antimicrobial agent is contemplated for use in the traumatic wound dressing system of the present disclosure. The use of antimicrobial agents is further demonstrated and described in the following documents, all of which are incorporated by reference to the extent they do not conflict herewith: U.S. Patent Application Publication No. 2007/0048344 to Yahiaoui, et al.; U.S. Patent Application Publication No. 2007/0048345 to Huang, et al.; U.S. Patent Application Publication No. 2007/0048356 to Schorr, et al., U.S. Patent Application Publication No. 2006/0140994 to Bagwell, et al.; U.S. Pat. No. 8,203,029 to Gibbins, et al.; and U.S. Pat. No. 8,551,517 to Hoffman, et al.

Particular antimicrobial agents contemplated by the present disclosure are discussed in more detail below.

Polyhexamethylene Biquanide (PHMB)

One antimicrobial agent contemplated for use in the traumatic wound dressing system of the present disclosure is polyhexamethylene biguanide (PHMB). PHMB (i.e., polihexanide) is an antiseptic that can be used wound care applications, although it has a long history of being used in cosmetics, for example in contact lens cleaning solutions, wet wipes, and the like. PHMB is available both as a cleansing solution (PRONTOSAN™, B. Braun) and in biocellulose dressings such as SUPRASORB™ X+PHMB (Lohmann and Rauscher). At a concentration of 0.3% (for example, in SUPRASORB™ X+PHMB) and of 0.1% (for example, in PRONTOSAN™), PHMB has proved to be non-cytotoxic and non-irritant, with a very low risk of sensitization. PHMB has been found to be effective against a broad spectrum of bacteria, aerobic as well as anaerobic, and also against fungi, molds, and yeasts, and has a proven effect against methicillin-resistant *Staphylococcus aureus* (MRSA) and vancomycin-resistant enterococcus (VRE).

Tests have been performed on *Staphylococcus aureus* to investigate the potential risks of this bacterium developing resistance to PHMB; the risk was found to be very low. An additional positive influence on the inflammatory process of wound healing, especially in infected or critically colonized wounds, has been the binding of inflammatory parameters such as free radicals, which demonstrates PHMB's antioxidative potential. The clinical effect of using PHMB in some non-healing wounds has been promising.

PHMB is a linear polymer comprised of a hydrophobic backbone with attached chains that make it highly water soluble. It is active against both gram-negative and gram-positive bacteria, as well as fungi. This activity is not generally affected by production of betalactamase by microorganisms, or by organic matter such as serum, blood, or wound fluid. The broad spectrum activity of PHMB has been demonstrated in studies with gauze dressings containing PHMB. PHMB is a membrane-active agent whose antimicrobial effect depends on disruption of the microbial cytoplasmic membrane and leakage of macromolecular components. The molecule binds to the surface of the bacterial cell membrane and causes reorganization of the membrane in a manner that prevents removal of the antimicrobial agent. This mode of action makes it unlikely that microorganisms can develop resistance.

Studies have compared treatment with a polihexanide-containing biocellulose wound dressing (BWD+PHMB) versus silver dressings (Ag) in painful, critically colonized (wounds-at-risk) or locally-infected wounds. Both BWD+PHMB and AG have been shown to be effective in reducing pain and bacterial burden. However, BWD+PHMB was significantly faster and better in removing the critical bacterial load, which such a dressing an attractive therapeutic option separately or in conjunction with silver to treat critically colonized and locally-infected wounds.

The use of PHMB as an antimicrobial agent is further demonstrated and described in the following documents, all of which are incorporated by reference to the extent they do not conflict herewith: U.S. Patent Application Publication No. 2007/0048344 to Yahiaoui, et al.; U.S. Patent Application Publication No. 2007/0048345 to Huang, et al.; U.S. Patent Application Publication No. 2007/0048356 to Schorr, et al; U.S. Patent Application Publication No. 2006/0147502 to Koenig, et al; U.S. Patent Application Publication No. 2007/0134303 to Yahiaoui, et al.; U.S. Patent Application Publication No. 2009/0014009 to Chen, et al.; U.S. Patent Application Publication No. 2006/0067964 to Koenig, et al.; U.S. Patent Application Publication No. 2009/0099532 to Cuevas, et al.; U.S. Patent Application Publication No. 2009/0099531 to Griesbach, III, et al.; U.S. Patent Application Publication No. 2007/0149435 to Koenig, et al.; U.S. Patent Application Publication No. 2010/0190004 to Gibbins, et al.; U.S. Patent Application Publication No. 2007/0044801 to Mathis, et al.; and U.S. Patent Application Publication No. 2006/0140994 to Bagwell, et al.

Chlorhexidine

Another antimicrobial agent or antiseptic contemplated for use in the traumatic wound dressing system of the present disclosure is chlorhexidine, which is a biguanide antiseptic. Chlorhexidine has been commonly used in disinfectant and antiseptic solutions. Chlorhexidine antiseptic solutions are used mainly in urology, gynecology, dentistry, and in the treatment of wounds. It is highly bactericidal. Concentrations around 0.02% can be used for wound irrigation. In other studies, chlorhexidine has been shown to decrease wound healing time. Chlorhexidine rinses have also been shown to be effective in reducing microbial complications when used perioperatively. It is produced in two forms: a 0.05% dilution for wound cleansing and a 4% solution for use as a surgical skin preparation and hand scrub. Recently, 2% solutions have been made available for surgical skin preparation.

Chlorhexidine gluconate (CHG) has been used for more than 30 years in the clinical setting. It has a high level of antimicrobial activity, low toxicity, and strong affinity for binding to the skin and mucous membranes. It can impart its antimicrobial activity at the membrane level, damaging both outer and inner bacterial membranes, causing leakage and possibly disrupting membrane potentials critical for ATP generation. It disrupts the microbial cell membrane and precipitates the cell contents. CHG at a concentration between 0.5% and 4% is more effective against gram-positive than gram-negative bacteria and has less activity against fungi and tubercle bacilli. It is inactive against bacteria spores, except at elevated temperatures. Numerous studies indicate that CHG is not absorbed through the skin and has a low skin irritancy potential. However, CHG should not come into contact with eyes, the middle ear, or meninges.

The use of CHG as an antimicrobial agent is further demonstrated and described in the following documents, all of which are incorporated by reference to the extent they do not conflict herewith: U.S. Patent Application Publication No. 2007/0048345 to Huang, et al.; U.S. Patent Application Publication No. 2004/0120915 to Yang, et al.; U.S. Patent Application Publication No. 2006/0003649 to Runge, et al.; U.S. Patent Application Publication No. 2006/0036222 to Cohen, et al.; U.S. Patent Application Publication No. 2006/0036223 to Baldwin, et al.; and U.S. Patent Application Publication No. 2006/0140994 to Bagwell, et al.

Silver

Another antimicrobial agent contemplated for use in the traumatic wound dressing system of the present disclosure is silver. The therapeutic potential of silver has long been recognized. Due to the broad bactericidal action of silver and the understanding that wound healing is impaired when bacterial levels surpass a particular threshold, multiple silver-based products have been developed to aid in wound healing. Such products incorporate silver into topical creams (silver sulfadiazine or Silvadene; King Pharmaceuticals, Bristol, Tenn.) or within various types of dressings, including foams (Contreet Ag; Coloplast, Marietta, Ga.), hydrocolloids (Contreet H; Coloplast, Marietta, Ga.), hydrofibers (AQUACEL™ Ag; Covatec, Skillman, N.J.), alginates (SILVERCEL™; Systagenix, Quincy, Mass.), film polymers (ARGLAES™; Medline, Mundelein, Ill.), or a polyethylene mesh with nanocrystalline silver (ACTICOAT™ Flex 7; Smith and Nephew, Hull, UK). These products work through the release of reactive silver cations, [Ag+], which may disrupt components of the bacterial cell wall, inhibit microbial respiratory enzymes and elements of the electron transport chain, and impair the synthesis and function of DNA and RNA.

The use of silver as an antimicrobial agent is further demonstrated and described in the following documents, all of which are incorporated by reference to the extent they do not conflict herewith: U.S. Patent Application Publication No. 2007/0003603 to Karandikar, et al.; U.S. Patent Application Publication No. 2012/0322903 to Karandikar, et al.; U.S. Patent Application Publication No. 2002/0006887 to Radwanski, et al.; U.S. Patent Application Publication No. 2004/0010215 to Gibbins, et al.; U.S. Patent Application Publication No. 2007/0293800 to McMaken, et al.; U.S. Patent Application Publication No. 2009/0035342 to Karandikar, et al; U.S. Patent Application Publication No. 2012/0183674 to Bonn-Savage, et al; U.S. Patent Application Publication No. 2007/0254044 to Karandikar, et al.; U.S. Patent Application Publication No. 2013/0164334 to Quincy, III, et al.; U.S. Patent Application Publication No. 2012/0240728 to Gann, et al.; U.S. Pat. No. 4,856,504 to Yamamoto, et al.; U.S. Patent Application Publication No. 2002/0022050 to Anderson, et al.; U.S. Patent Application Publication No. 2004/0120921 to Quincy, III, et al.; U.S. Pat. No. 6,797,856 to Kolb, et al.; U.S. Patent Application Publication No. 2006/0003649 to Runge, et al.; U.S. Pat. No. 6,020,047 to Everhart; U.S. Patent Application Publication No. 2005/0058711 to Massengale, et al.; U.S. Patent Application Publication No. 2011/0135702 to Hoffman, et al.; U.S. Patent Application Publication No. 2005/0148490 to Krzysik, et al.; U.S. Patent Application Publication No. 2008/0132438 to Hoffman, et al.; U.S. Patent Application Publication No. 2003/0203009 to MacDonald; U.S. Patent Application Publication No. 2010/0190004 to Gibbins, et al.; U.S. Pat. No. 5,599,585 to Cohen; and U.S. Patent Application Publication No. 2007/0044801 to Mathis.

b. Hemostatic Agents

Hemostatic agents are also contemplated for use in the traumatic wound dressing system of the present disclosure and can be used to deliver blood loss prevention and/or coagulation benefits. Useful hemostatic agents include polyacrylate polymers, modified clays, and $CaCl_2$ in a polyacrylate polymer matrix. The use of these and other hemostatic agents is further demonstrated and described in the following documents, all of which are incorporated by reference to the extent they do not conflict herewith: U.S. Pat. No. 7,335,713 to Lang, et al.; and U.S. Pat. No. 6,822,135 to Soerens, et al.

c. Toxin Sequestration Agents

Toxin sequestration agents are also contemplated for use in the traumatic wound dressing system of the present disclosure. Toxin sequestration agents include modified clay technology, as well as any other agents that reduce or eliminate biotoxin interaction with the wound and the surrounding tissue. The use of these and other toxin sequestration agents is further demonstrated and described in the following documents, all of which are incorporated by reference to the extent they do not conflict herewith: U.S. Pat. No. 6,551,607 to Minerath, III, et al.; U.S. Pat. No. 6,521,241 to Minerath, III, et al.; U.S. Pat. No. 6,485,733 to Huard, et al.; U.S. Pat. No. 6,517,848 to Huard, et al.; and U.S. Pat. No. 8,110,215 to Koenig, et al.

d. Pain Medication

Pain medications are well known, and any suitable topical, local, or systemic pain medication known in the art can be used in the traumatic wound dressing system of the present disclosure. Suitable examples include but are not limited to lidocaine, benzocaine, or prilocaine.

e. Debridement Agents

The traumatic wound dressing system of the present disclosure also contemplates the use of one or more debridement agents. Debridement upon reaching an aid station can be enhanced by using debridement agents. Classes of such debridement agents include structured surfactant technology and agents that allow cleaning and debridement of the wound and the surrounding tissue. The use of these and other debridement agents is further demonstrated and described in the following documents, all of which are incorporated by reference to the extent they do not conflict herewith: U.S. Pat. No. 7,268,104 to Krzysik et al.; U.S. Pat. No. 7,666,824 to Krzysik, et al.; U.S. Pat. No. 8,545,951 to Yahiaoui, et al.; and U.S. Pat. No. 6,764,988 to Koenig, et al.

f. Modified Clay

The traumatic wound dressing system of the present disclosure also contemplates the use of a modified clay. The use of modified clays is further demonstrated and described in the following documents, all of which are incorporated by reference to the extent they do not conflict herewith: U.S. Pat. No. 6,551,607 to Minerath, III, et al.; U.S. Pat. No. 6,521,241 to Minerath, III, et al.; U.S. Pat. No. 6,517,848 to Huard, et al.; and U.S. Pat. No. 6,485,733 to Huard, et al. In some embodiments, the clays can be organophilically or non-organophilically modified. By an organophilically modified clay it is meant that the naturally occurring charge has been significantly reduced by adding relatively hydrophobic material to the surface of the native material. For instance, modifications to clays have been accomplished using a variety of techniques including derivatization with phenolic, quaternary ammonium, methyl methacrylate compounds. For example, a quaternary ammonium compound that can be used in preparing the organophilic modified clay component of the traumatic wound dressing of the present disclosure can have one or two long-chain substituents, e.g., 14-20 carbon atoms, and two or three short-chain substituents such as methyl groups. One particularly suitable quaternary ammonium compound is dimethyl dihydrogenated tallow ammonium chloride. Because the tallow contains a large proportion of stearic acid, which contains 18 carbon atoms, the resulting clay is often referred to as a quaternium 18 clay, e.g., quaternium 18 bentonite, or quaternium 18 hectorite. The composition and preparation of such organophilic clays is well-known. In one embodiment, the modified organophilic clay for use in the present disclosure is quaternium 18 bentonite. Meanwhile, non-organophilically modified clays are formed by minor other processing modifications, such as the addition of inorganic counter ions, such as mono- and di-valent cations, e.g. lithium, sodium or potassium.

2. Liquid

In addition to including a bioactive powder component, the traumatic wound dressing system of the present disclosure also includes a liquid component. Prior to use of the traumatic wound dressing system to cover a wound site, the bioactive liquid can be contained in the frangible ampoule or any other suitable containment device in the center of the wrap of the traumatic wound dressing of the present disclosure. The ampoule or other containment device can be ruptured or otherwise opened so that the liquid can saturate the wrap before application of the wrap to a wound site.

In one embodiment, the liquid can be released when the canister twist cap is twisted to facilitate the release and application of the bioactive powder to the wound to be treated. The liquid can include one or more of hemostatic agents, antimicrobial agents, biotoxin sequestrants, pain medication, debridement agents, and precursors for oxygen generation (e.g., a reactant such as a peroxide). Hemostatic agents, antimicrobial agents, biotoxin sequestrants, pain medication, and debridement agents are described above with respect to the bioactive powder. In some embodiments, it is contemplated that the liquid component may include a biocompatible carrier for certain ingredients. For example, one or more ingredients may be incorporated into, integrated with, or included in a biocompatible carrier that may be blended or included in the liquid, and the biocompatible carrier itself may have bioactive properties.

The main functions of the liquid present in the ampoule is to provide oxygen to the wound site, to minimize infection at the wound site, and to allow for rapid and complete debridement of the wound site at a later time. In one embodiment, the liquid can be formulated using FDA-approved ingredients and can include one or more of hydrogen peroxide (such as 3.3% hydrogen peroxide), cationic surfactants, stabilizing agents, thickening agents, and preservatives. The liquid composition can also include a hemostatic agent and pain medication such as a local analgesic. The various components of the liquid are described below in Table 2.

oxygen precursor liquid that is introduced upon rupture of the frangible ampoule comes into contact with the wrap, as discussed in more detail below. In another embodiment, the oxygen catalyst can be any other suitable oxygen catalyst such as a carbonate (e.g., sodium bicarbonate), a copper compound, catalase, peroxidase, manganese dioxide, iodide, or potassium iodine, for example.

Figure 3:
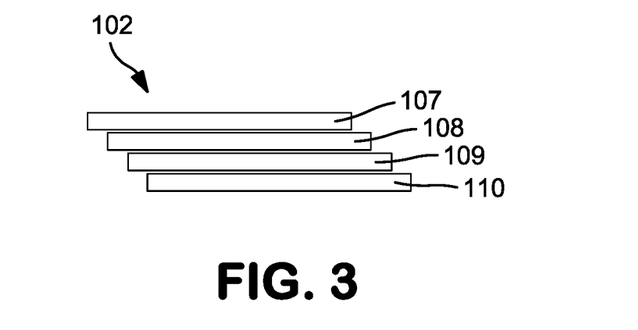
FIG. 3 schematically illustrates one embodiment of a wrap that may be a part of the wound dressing system of FIG. 1.

The elastic wrap can be a multilayer nonwoven composite material that provides properties similar to woven LYCRA™ fabrics, with the durability and cost of a nonwoven material. The components of the wrap are illustrated in FIG. 3. For example, the wrap 102 can be a nonwoven composite that includes a skin or mucosa contacting inner absorbent layer 107, and an outer protective layer 110, where the absorbent layer 107 contacts a wound site and the

TABLE 2

Description and Function of Bioactive Liquid Components

| Ingredient | Function | Core Technology |
| --- | --- | --- |
| Hydrogen Peroxide | Precursor for Oxygen Generation | U.S. Pat. No. 7,160,553<br>U.S. Pat. No. 7,235,263 |
| Structured Surfactants | Active Migration Aid<br>Debridement Aid | U.S. Pat. No. 7,666,824 |
| Sorbitol or Mannitol | Hydrogen Peroxide Stabilizer | U.S. Pat. No. 7,235,263 |
| Polyhexamethylene Biguanide (PHMB) | Preservative<br>Antimicrobial | U.S. Pat. No. 8,551,517<br>U.S. Pat. App. Pub. No. 2007/0048345<br>U.S. Pat. App. Pub. No. 2010/0190004 |
| Biocompatible Carrier | Rheology Modifier<br>Absorbent<br>Moisture Control | U.S. Pat. No. 7,335,713<br>U.S. Pat. No. 6,822,135<br>U.S. Pat. No. 8,679,523<br>U.S. Pat. No. 8,901,188<br>U.S. Pat. App. Publication No. 2012/265124<br>PCT/US2014/067530<br>Caprolactone Urethane<br>Poly(lactic Acid) Diol Urethane<br>Poly(ethylene glycol) Urethane<br>Hydroxybutyric acid urethane |
| Sodium Carbonate | Neutralizer | — |
| Citric Acid | pH Modifier | — |
| Optional Microencapsulated Delivery Vehicle | Optional Encapsulation of hydrogen peroxide | U.S. Pat No. 8,192,841<br>U.S. Pat. App. Pub. No 2007/0148459 |
| Optional Aluminum Chloride, Kaolinite, Mineral Zeolite, or Microfibrillar Collagen | Optional OTC Topical Hemostatic Agents | DRYSOL ™ and XERAC ™ AC by Person & Covey<br>CERTAINDRI ™ by DSE Healthcare<br>AVITENE ™ Flour by Davol<br>HELITENE ™ by Integra<br>INSTAT ™ by Ethicon |
| Optional Lidocaine, Benzocaine, or Prilocaine | Optional OTC Local Analgesic | BIOPELLE ™ by Ferndale Laboratories |
| Optional Modified Clay | Optional Rheology Modifier<br>Anti-Caking Agent<br>Biotoxin Sequestration | U.S. Pat. No. 6,485,733<br>U.S. Pat. No. 6,517,848 |

3. Wrap

In addition to including a bioactive powder component and a bioactive liquid component, the traumatic wound dressing system of the present disclosure also includes a wrap. The wrap or dressing can be absorbent and can have elastic properties that provide enhanced compression benefits by applying pressure to immobilize the wound site and minimize minor bleeding. In one embodiment, the wrap can be in the form of a nonwoven composite. As discussed above, an adhesive strip can be provided at one end of the wrap to allow for ease of initial placement on healthy tissue. In one embodiment, the wrap can be impregnated with a nanoparticle metal (e.g., nanoparticle silver), which can serve as an oxygen catalyst to generate oxygen when the outer protective layer 110 is exposed to the outside environment upon application of the wrap 102 to a wound site. Further, the wrap 102 can also include a breathable barrier layer 108 and an elastic layer 109.

Additionally, as mentioned above, the wrap can be treated in a converting process with nanoparticle metal (e.g., nanoparticle silver), and can also be treated with various surfactants, etc. to tailor the functionality of this material for optimum battlefield use.

The various wrap 102 components that may be include in the traumatic wound dressing system of the present invention are described in Table 3 below.

TABLE 3

Description and Function of Components of a Multilayer Wrap

| Component | Function | Core Technology |
|---|---|---|
| Absorbent wicking layer | Control bleeding<br>Physically protect | U.S. Pat. No. 6,103,647<br>U.S. Pat. App. Pub. No. 2003/0040691 |
| Breathable/barrier layer | Water/air transfer<br>Moisture balance | U.S. Pat. App. Pub. No. 2008/0108268<br>U.S. Pat. No. 6,794,024<br>U.S. Pat. No. 6,045,900 |
| Elastic layer | Compression<br>Conformability | U.S. Pat. App. Pub. No. 2003/0040691<br>U.S. Pat. No. 6,015,764<br>U.S. Pat. No. 6,111,163 |
| Outer protective layer | Tensile strength, tear and puncture resistance<br>Controlled moisture barrier | U.S. Pat. App. Pub. No. 2008/0108268<br>U.S. Pat. No. 6,045,900 |
| Nanoparticle Metal (e.g. nanoparticle silver) | Catalyst to generate oxygen<br>microbial control | U.S. Pat. No. 8,203,029<br>U.S. Pat. No. 8,361,553<br>U.S. Pat. No. 7,576,255<br>U.S. Pat. App. Pub. No. 2004/0010215 |
| Surfactant | Wettability | U.S. Pat. No. 7,666,824 |

The outer protective layer 110 can provide tensile strength and tear and puncture resistance with adjustable coverage area. The wrap can provide adjustable levels of compression force due to the retraction forces inherent in the elastic components of the web. The composite provides comfort and conformability to control bleeding, physically protect the wounded limb, and preserve injured tissue. The outer protective layer 110 further protects against bacteria and solid particle penetration through size exclusion, reducing the risk of infection from the environment and the spread of bacteria from the wound to the surrounding area.

Meanwhile, the skin contacting, inner absorbent layer 107 of the wrap, which is the layer of the wrap positioned adjacent the wound site, provides optimum air and water vapor transport, delivering comfort and thermal management while providing absorbency to control of minor bleeding and wound exudate management. The absorbent layer 107 of the composite can be coated with surfactants to enhance diffusion of the liquid hydrogen peroxide from the frangible ampoule to the trapped nanoparticle metal (e.g., nanoparticle silver) that may be present on the wrap. The surfactant coating can also allow for direct migration of exudates to the absorbent core. Additionally, the inner absorbent layer 107 can be tailored such that it is non-stick to skin or mucosa.

The combination of the outer protective layer 110 and the inner absorbent layer 107 can ultimately provide a soft, lint-free, non-irritating feel against skin and mucosa. Further, it is to be understood that both the outer protective layer 110 and the inner absorbent layer 107, and any layers positioned there between, can be impregnated with nanoparticle metal (e.g., nanoparticle silver) which can be employed as a catalyst to generate oxygen from a liquid precursor (e.g., a reactant such as peroxide) introduced before the wrap 102 is applied to a wound site. Furthermore, when nanoparticle silver is utilized in such layers, it provides for additional protection against microbial contamination as described above. The catalytic reaction of the hydrogen peroxide with silver occurs at the location of the nanoparticles trapped in the wrap 102. The silver that is released for antimicrobial action is at levels below that associated with argyria due to the dissolution rate design of the silver nanoparticles.

The wrap 102 and its components are further demonstrated and described in the following documents, all of which are incorporated by reference to the extent they do not conflict herewith: U.S. Pat. No. 8,475,560 to Gann, et al.; U.S. Pat. No. 8,293,965 to McMaken, et al.; U.S. Pat. No. 7,642,397 to Cohen, et al.; U.S. Pat. No. 7,422,712 to DeLucia, et al.; U.S. Pat. No. 5,030,375 to Sigl, et al.; U.S. Patent Application Publication No. 2002/0111576 to Greene, et al.; U.S. Patent Application Publication No. 2003/0127767 to Potts, et al.; U.S. Patent Application Publication No. 2007/0141130 to Villaneuva, et al.; U.S. Pat. No. 6,348,258 to Topolkaraev, et al.; U.S. Pat. No. 4,798,603 to Meyer, et al; U.S. Pat. No. 6,172,276 to Hetzler, et al.; U.S. Pat. No. 6,627,564 to Morman, et al.; U.S. Patent Application Publication No. 2001/0031938 to DeLucia, et al.; U.S. Patent Application Publication No. 2014/0276513 to MacDonald, et al.; U.S. Patent Application Publication No. 2007/0003603 to Karandikar, et al.; U.S. Patent Application Publication No. 2012/0322903 to Karandikar, et al.; U.S. Patent Application Publication No. 2002/0006887 to Radwanski, et al.; U.S. Patent Application Publication No. 2004/0010215 to Gibbins, et al.; U.S. Patent Application Publication No. 2007/0293800 to McMaken, et al.; U.S. Patent Application Publication No. 2009/0035342 to Karandikar, et al.; U.S. Patent Application Publication No. 2012/0183674 to Bonn-Savage, et al.; U.S. Patent Application Publication No. 2007/0254044 to Karandikar, et al.; and U.S. Patent Application Publication No. 2010/0190004 to Gibbins, et al.

4. Oxygen Generation

Another feature of the traumatic wound dressing system of the present disclosure is the ability of the system to generate oxygen within the wrap and then subsequently deliver this oxygen to the wound and the surrounding tissue.

The oxygenation needs of the human skin are typically met by the combination of direct oxygen uptake from the ambient air and by tissue oxygenation from the vasculature. Dissolved oxygen is essential at all stages of the wound healing process. Poor tissue oxygenation can result in impaired healing. Chronic wounds are notably hypoxic, with an oxygen tension of 5 to 20 mmHg, compared to an oxygen tension of 30 to 50 mmHg in healthy tissue. In healing tissue, oxygen is required as a substrate for the production of biological energy, resistance to infection, collagen synthesis, blood vessel formation, cell migration, and cell proliferation. In addition, oxygen also serves as a signaling molecule to initiate cell motility and enhance the expression of several pro-inflammatory and angiogenic growth factors. In the human skin, adequate oxygen supply is a balance between proper oxygen transport by the blood and direct uptake from the atmosphere. Therefore, oxygen delivery to the wound is dependent on multiple factors including blood perfusion of the tissue, capillary density, arterial partial oxygen pressure (poxygen), the blood hemoglobin level, and local oxygen consumption. Oxygen is not stored in the tissue and several systemic conditions, including advancing age and diabetes, can endanger its availability. Consequently, it is imperative that upon injury, the healing tissue quickly adapts to continuously meet the oxygen requirements for proper healing and repair. Although the wounded tissue demands high oxygen levels, the overall oxygen needs of a wound differ at the different stages of the wound healing process.

Healthy tissue needs to be able to adjust oxygen delivery when there is an increase in oxygen demand. In the human skin oxygen delivery occurs by diffusion via direct uptake from the atmosphere and from the vasculature, where the oxygen moves from areas of high concentration to areas of low concentration. Satisfactory oxygen supply to the subcutaneous tissue is highly dependent on appropriate oxygen transport through the blood at a sufficient bulk flow rate. During tissue injury, blood supply decreases due to disruption of blood vessels. As a consequence, there is a marked decrease in oxygen delivery. Although the wounded tissue is equipped with all the necessary tools to repair the damage and restore blood supply, there are intrinsic and extrinsic factors that can impair this process, resulting in prolonged oxygen deficiency or chronic tissue hypoxia. Because adequate oxygen supply is essential for successful tissue repair, inability of the wounded tissue to meet oxygen demand can be pathological, resulting in cell death and tissue necrosis.

Therefore, the goal of an oxygen-based therapy for wound care is to fulfill the oxygen demand of the healing tissue and maintain an oxygen concentration near an oxygen tension of about 40 mmHg, which is the average oxygen tension found in healthy, well-perfused tissues. Delivery of oxygen as part of oxygen-based therapy has been used clinically as an effective therapy for wound healing since the 1960s with the administration of systemic hyperbaric oxygen (HBO).

Throughout the years, advancements have been made in the scientific field to improve oxygen-based therapies for wound healing. In recent years, new oxygen delivery technologies have emerged that aim to locally provide oxygen to the wounded tissue at a faster and more efficient way than HBO therapy via topical administration. Clinical results have shown that topical delivery of oxygen to the wounded tissue can enhance the rate of epithelialization, induce extracellular matrix protein synthesis, and the expression of angiogenic factors. It should be understood that topically-delivered oxygen only targets the wounded tissue and, as a result, it does not involve high pressure and does not risk the potential for systemic oxygen toxicity.

Figure 4:
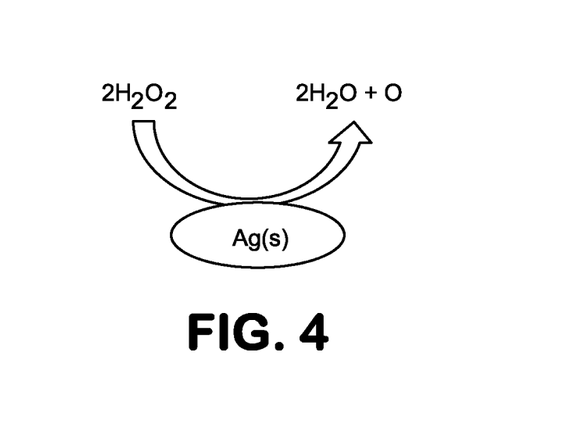
FIG. 4 illustrates the oxygen production associated with a silver-nanoparticle-impregnated wrap contemplated by the wound dressing system of FIG. 1.
Figure 5:
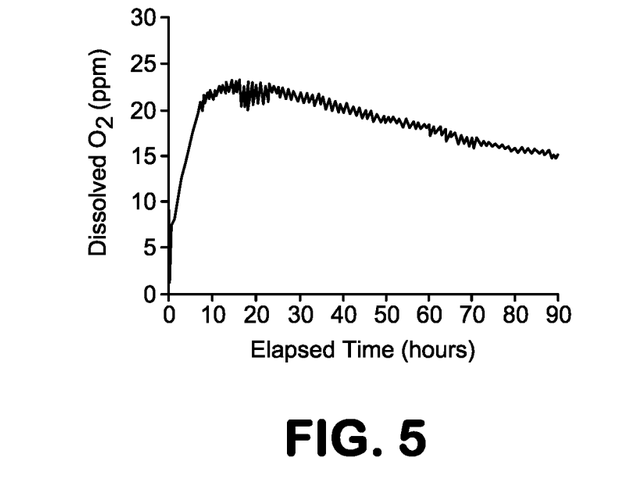
FIG. 5 illustrates the hydrogen peroxide generated oxygen release as a function of time from a polyacrylate polymer.

A wound dressing product as described in U.S. Pat. No. 7,160,553 to Gibbins, et al. and U.S. Pat. No. 8,679,523 to Gibbins, et al. and sold under the name OXYGENESYS™ has been developed that can deliver dissolved oxygen to the wound over an extended period. In this product, oxygen is produced by mixing a reactant (i.e., oxygen precursor) with an oxygen catalyst. The oxygen generation system used in the present application can employs hydrogen peroxide ($2H_2O_2$) as the reactant and silver nanoparticles Ag(s) as the catalyst to produce water ($2H_2O$) and oxygen ($O_2$), as illustrated in FIG. 4, although any other suitable reactant/catalyst combination as discussed in U.S. Pat. No. 7,160,553 to Gibbins, et al. and U.S. Pat. No. 8,679,523 to Gibbins, et al. is contemplated by the present disclosure. Both the nanoparticle silver on the surface of the wrap and the silver ions released serve to convert the hydrogen peroxide into oxygen. An example of this process has shown that oxygen generated by the catalytic conversion of hydrogen peroxide incorporated into a polyacrylate polymer can be released for over 80 hours, as illustrated in FIG. 5. The hydrogen peroxide reactant acts as an oxygen precursor. Other useful oxygen precursors include mannitol peroxide, urea peroxide, organic peroxides, and combinations thereof. Meanwhile, in addition to a nanoparticle metal (e.g., nanoparticle silver), other suitable oxygen catalysts can include a carbonate (e.g., sodium bicarbonate), a copper compound, catalase, peroxidase, manganese dioxide, iodide, potassium iodine, etc.

Such a chemistry is employed in the traumatic wound dressing system of the present application. When the system is deployed, oxygen will be generated and trapped between the wound and the hydrogel formed by the bioactive powder. The material design of the hydrogel resulting from coating or spraying the bioactive powder on a wound site as well as the design of the wrap ensure that the oxygen will be delivered to the wound over an extended period of time. Although nanoparticle silver has been primarily discussed above, it is to be understood that any other suitable catalyst can be used in the traumatic wound dressing system of the present disclosure. For instance, the catalyst used to generate oxygen can be one or more of other metallic nanoparticles including copper, zinc, nickel, and gold. The use of silver, including silver nanoparticles, as the catalyst also serves the purpose of an additional antimicrobial, as described above.

The wound dressing system of the present disclosure also contemplates the use of a polyacrylamide-based matrix that can release and deliver both dissolved oxygen and silver. The matrix is available as a conformable gel patch or foamed gel and is sold under the OXYGENESYS™ brand name. Other polyacrylic acid-based hydrogel matrices employed herein demonstrate delivery of dissolved oxygen, silver, and bioactives. On contact with the wound surface, the matrix can form a viscous hydrogel allowing for an increased and more consistent concentration of dissolved oxygen to be delivered to the wound bed over many hours.

The polyacrylic acid-based gel can also be converted into a flowable powder, allowing it to be applied to a wound site in dry, powdered form. The unique benefits of the powder is that it can be applied to most wound shapes and depths and quickly sets up as a flexible barrier by absorbing the wound exudate and forming a hydrogel seal on the wound bed. This hydrogel also maintains a good balance of moisture in the wound bed. The hydrogel powder can also deliver dissolved oxygen, antimicrobials, and/or other bioactives as discussed above for wound preservation and healing. When the wound dressing system is removed after use, the powdered hydrogel coating can be easily removed by gentle irrigation of the wound area with gravity fed saline.

An advantage of the oxygen-generating technology described herein is that it can supply continuous oxygen to the wound in a form that has already crossed the gas to liquid interface (as the free, unbound oxygen found in plasma), thus making it readily available for cell consumption. This oxygen-generating technology has proven effective in the transcutaneous delivery of dissolved oxygen beyond a 700 µm thickness of viable human skin, achieving a penetration oxygen level twice the depth of that observed for hyperbaric gaseous oxygen therapy. Furthermore, this technology has shown to positively affect various phases of the wound healing process. Specifically, this oxygen-generating technology has been found to reduce dermal and subcutaneous inflammation as well as bacterial burden in ischemic porcine wounds. Such oxygen-generating technology can also reduce dermal fibrosis and necrosis. Further, this oxygen-generating technology can promote healing when applied to chronic venous stasis ulcers, dehiscent surgical closures, pressure ulcers, and skin flaps. Furthermore, delivery of dissolved oxygen by this oxygen-generating technology wound dressing system can facilitate increase in collagen type I, elastin and fillagrin, in addition to down-regulating inflammatory cytokines and matrix metalloproteinases 1 and 12.

This oxygen-generating technology is further demonstrated and described in the following documents, all of which are incorporated by reference to the extent they do not conflict herewith: U.S. Pat. No. 8,679,523 to Gibbins, et al.; U.S. Pat. No. 7,160,553 to Gibbins, et al.; U.S. Pat. No. 7,235,263 to Koenig, et al.; and U.S. Pat. No. 6,887,496 to Koenig, et al.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A wound dressing system comprising:
    a canister;
    a powder disposed within the canister, wherein the canister is configured to allow the powder to be dispersed onto a wound site when the canister is activated; wherein activating the canister comprises squeezing or compressing the canister; a wrap disposed in the canister and separated from the powder, wherein the wrap is configured to contact or surround the wound site;
    an oxygen catalyst; and
    a frangible ampoule disposed in the canister and including a liquid containing an oxygen precursor, wherein the liquid is configured to contact the wrap upon activation of the canister, wherein the oxygen catalyst and the oxygen precursor are configured to form oxygen when combined.

2. The system of claim 1, wherein the powder includes a hemostatic agent, an antimicrobial agent, a biotoxin sequestrant, pain medication, a debridement agent, an oxygen catalyst, or a combination thereof.

3. The system of claim 1, wherein the liquid includes a hemostatic agent, an antimicrobial agent, a biotoxin sequestrant, pain medication, a debridement agent, or a combination thereof.

4. The system of claim 1, wherein the wrap includes an inner absorbent layer, wherein the inner absorbent layer is positioned adjacent the wound site when the wrap is applied to the wound site, further wherein the wrap includes an outer protective layer.

5. The system of claim 1, wherein the wrap includes an elastic layer, a breathable barrier layer, or a combination thereof.

6. The system of claim 1, wherein an end of the wrap includes an adhesive.

7. The system of claim 1, wherein the wrap is a nonwoven composite.

8. The system of claim 1, wherein the wrap includes the oxygen catalyst.

9. The system of claim 1, wherein the oxygen precursor includes a peroxide.

10. The system of claim 9, wherein the peroxide is hydrogen peroxide, mannitol peroxide, urea peroxide, or an organic peroxide.

11. The system of claim 1, wherein the oxygen catalyst includes a nanoparticle metal, a carbonate, a copper compound, catalase, peroxidase, manganese dioxide, iodide, potassium iodine, or a combination thereof.

12. The system of claim 11, wherein the nanoparticle metal is nanoparticle silver.

13. A method of applying a wound dressing system to a would site, the wound dressing system comprising a bioactive powder, a bioactive liquid, and a wrap, wherein the bioactive powder, the bioactive liquid, and the wrap are disposed within a container, the method comprising the steps of:
    squeezing or compressing the container to activate the container to disperse the bioactive powder onto the wound site, wherein the step of squeezing or compressing the container compresses a frangible ampoule inside the container to disperse the bioactive liquid;
    allowing sufficient time for the wrap to absorb the bioactive liquid, wherein the bioactive liquid includes an oxygen precursor and the wrap includes an oxygen catalyst, wherein oxygen is formed when the bioactive liquid contacts wrap; and
    wrapping the wrap around the wound site.

* * * * *